(12) United States Patent
Morita (10) Patent No.: US 9,568,720 B2
(45) Date of Patent: Feb. 14, 2017

(54) SURGICAL OBSERVATION SYSTEM FOR OBSERVING, IN THREE DIMENSIONS, A SURGICAL SITE FROM TWO DIRECTIONS

(71) Applicant: OLYMPUS CORPORATION, Tokyo (JP)

(72) Inventor: Kazuo Morita, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 14/956,575

(22) Filed: Dec. 2, 2015

(65) Prior Publication Data

US 2016/0095666 A1 Apr. 7, 2016

Related U.S. Application Data

(63) Continuation of application No. PCT/JP2014/083039, filed on Dec. 12, 2014.

(30) Foreign Application Priority Data

Dec. 20, 2013 (JP) ................................ 2013-264031

(51) Int. Cl.
*G02B 21/22* (2006.01)
*G02B 21/00* (2006.01)
(Continued)

(52) U.S. Cl.
CPC ....... *G02B 21/0012* (2013.01); *A61B 19/5212* (2013.01); *A61B 19/5223* (2013.01);
(Continued)

(58) Field of Classification Search
CPC ... G02B 21/00; G02B 21/004; G02B 21/0012; G02B 21/18; G02B 21/20; G02B 21/22
(Continued)

(56) References Cited

U.S. PATENT DOCUMENTS 5,668,661 A * 9/1997 Tomioka ................ G02B 21/18
359/368
5,729,382 A * 3/1998 Morita ............... G02B 27/0081
359/373
(Continued)

FOREIGN PATENT DOCUMENTS

JP H09-21962 1/1997
JP H10-39228 2/1998
(Continued)

OTHER PUBLICATIONS

International Search Report, dated Mar. 17, 2015, issued in corresponding International Application No. PCT/JP2014/083039.

*Primary Examiner* — Arnel C Lavarias
(74) *Attorney, Agent, or Firm* — Andrews Kurth Kenyon LLP (57) ABSTRACT

Surgical observation system for observing, in three dimensions, a surgical site from two directions are provided herein. The surgical observation system may include a first image-acquisition optical system that obtains, from a first observation direction, a pair of optical images, having parallax, of a subject via a pair of apertures disposed side-by-side; and a second image-acquisition optical system that obtains, from a second observation direction in which an angle about an optical axis differs from that of the first observation direction, another pair of optical images, having parallax, of a subject via another pair of apertures disposed side-by-side.

3 Claims, 9 Drawing Sheets

(51) Int. Cl.
 *G02B 21/02* (2006.01)
 *A61B 19/00* (2006.01)
(52) U.S. Cl.
 CPC ............ *A61B 90/361* (2016.02); *G02B 21/02* (2013.01); *G02B 21/22* (2013.01)
(58) Field of Classification Search
 USPC ....... 359/377, 362, 363, 368, 369, 372, 373, 359/374, 375, 376, 378
 See application file for complete search history.

(56) References Cited

U.S. PATENT DOCUMENTS

| | | | |
|---|---|---|---|
| 5,898,518 A * | 4/1999 | Biber ..................... | G02B 21/18 359/375 |
| 2004/0227989 A1* | 11/2004 | Obrebski ........... | G02B 21/0012 359/388 |
| 2011/0032607 A1* | 2/2011 | Abele ................... | A61B 90/20 359/376 |

FOREIGN PATENT DOCUMENTS

| | | |
|---|---|---|
| JP | 2004-287443 | 10/2004 |
| JP | 2008-36277 | 2/2008 |

* cited by examiner

SURGICAL OBSERVATION SYSTEM FOR OBSERVING, IN THREE DIMENSIONS, A SURGICAL SITE FROM TWO DIRECTIONS

CROSS-REFERENCE TO RELATED APPLICATIONS

This is a continuation of International Application PCT/JP2014/083039, with an international filing date of Dec. 12, 2014, which is hereby incorporated by reference herein in its entirety. This application claims the benefit of Japanese Patent Application No. 2013-264031, the content of which is incorporated herein by reference.

TECHNICAL FIELD

The present invention relates to surgical observation systems and, in particular, to surgical observation systems for three-dimensionally observing a surgical site from two directions.

BACKGROUND ART

In surgery, surgical observation systems have been proposed in which three-dimensional images are obtained from optical images of a surgical site with an image-acquisition optical system disposed at a desired position above the surgical site in a patient, and the obtained three-dimensional images are supplied to a lead surgeon (hereinafter simply referred to as "surgeon") and an assistant, who is an assistant surgeon (hereinafter simply referred to as "assistant"), via monitors. In particular, in neurosurgery, because the surgeon and the assistant are located so as to form an angle of 90° with respect to the patient, the observation directions from the surgeon and the assistant to the surgical site differ by 90°. Therefore, with the surgical observation system, the surgeon and the assistant are respectively provided with three-dimensional images of the surgical site as viewed from the direction of each person (see Patent Literature 1).

Since the surgeon and the assistant perform the operation on the patient while observing the three-dimensional images of the surgical site displayed on the monitors, the housing that accommodates the image-acquisition optical system must be as compact as possible so as not to hinder the surgical procedure or viewing of the monitors by the surgeon and assistant during the surgery.

In the case where the observation directions of the surgeon and the assistant differ, as described above, to provide three-dimensional images as viewed from the direction of each person, it is necessary to obtain three-dimensional images of the surgical site from two different directions. Thus, in the surgical observation system, two image-acquisition optical systems having a pair of apertures disposed side-by-side are made to intersect each other, and two image-acquisition optical systems formed of a total of four apertures must be accommodated in the housing, which makes the housing large. A large housing hinders the surgical procedure or viewing of the monitors by the surgeon and the assistant during surgery.

CITATION LIST

Patent Literature

{PTL 1}
Japanese Unexamined Patent Application, Publication No. HEI-9-21962

SUMMARY OF INVENTION

Solution to Problem

One aspect of the present invention is a surgical observation system including a first image-acquisition optical system that obtains, from a first observation direction, a pair of optical images, having parallax, of a subject via a pair of apertures disposed side-by-side; and a second image-acquisition optical system that obtains, from a second observation direction in which an angle about an optical axis differs from that of the first observation direction, another pair of optical images, having parallax, of the subject via another pair of apertures disposed side-by-side, wherein the areas of the apertures of the first image-acquisition optical system are larger than the areas of the apertures of the second image-acquisition optical system, and the first image-acquisition optical system and the second image-acquisition optical system are disposed so as to satisfy the following conditional expression.

$$0.4 \leq L2/L1 \leq 0.6 \tag{1}$$

Here, L1 is the distance between centers of the apertures of the first image-acquisition optical system, and L2 is the distance between centers of the apertures of the second image-acquisition optical system.

DESCRIPTION OF EMBODIMENT

A surgical observation system according to an embodiment of the present invention will be described below with reference to the drawings.

The surgical observation system provides both a surgeon and an assistant with respective three-dimensional images of a surgical site as viewed from the direction of each person during surgery which the surgeon and the assistant perform at positions forming a prescribed angle with respect to the patient.

Figure 1:
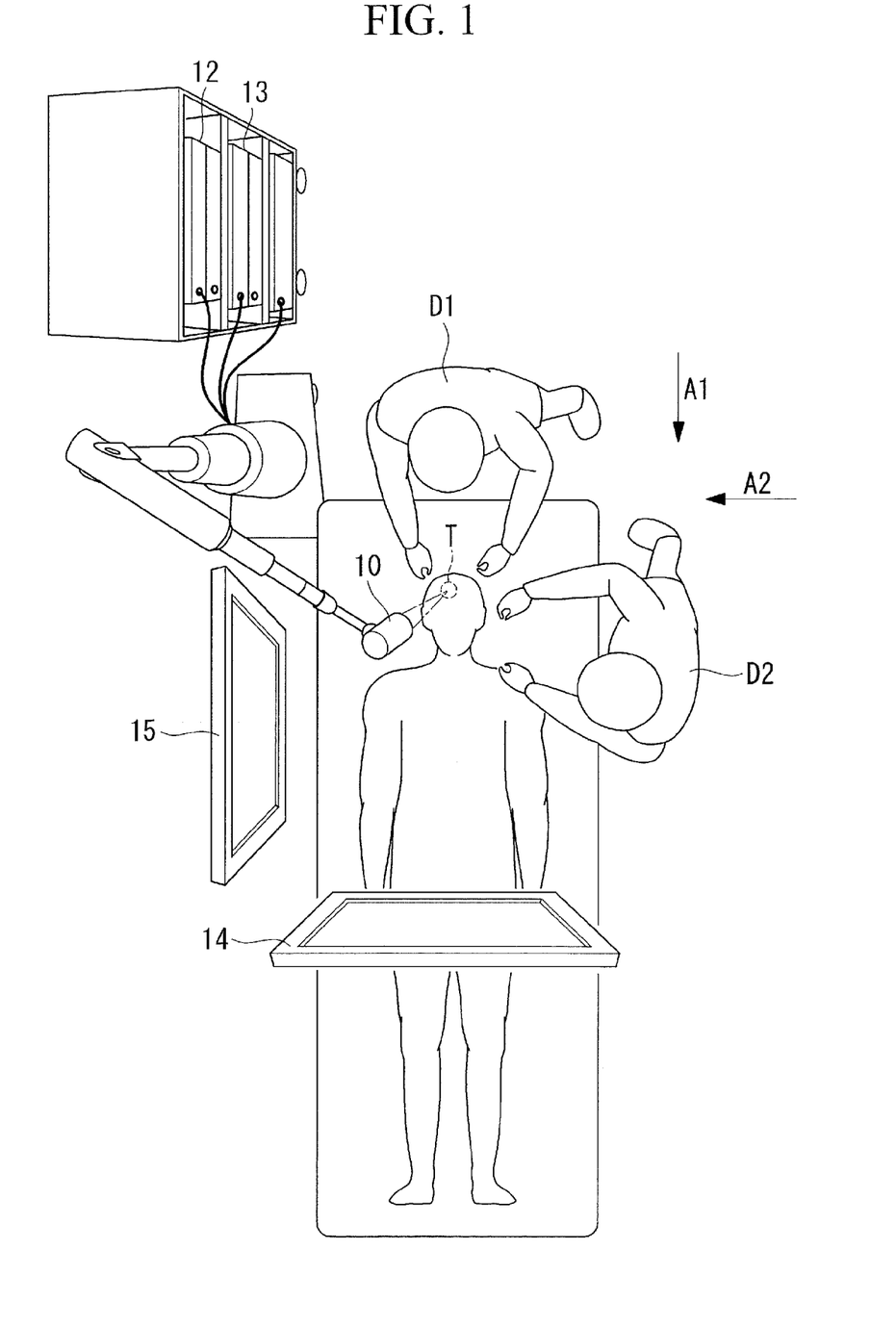
FIG. 1 is a diagram showing, in outline, the configuration of a surgical observation system according to an embodiment of the present invention.

As shown in FIG. 1, the surgical observation system includes a case (housing) 10 that is attached to the distal end of a support arm provided on a stand installed on the floor and that accommodates an image-acquisition optical system that collects light from a surgical site T in a patient; a surgeon video processor 12 that generates a three-dimensional image to be provided to a surgeon D1 from optical images acquired by an image-acquisition optical system built into the case 10; an assistant video processor 13 that generates a three-dimensional image to be provided to an assistant D2 in a similar manner; a surgeon monitor 14 that displays the three-dimensional image generated by the surgeon video processor 12 to provide it to the surgeon D1; and an assistant monitor 15 that displays the three-dimensional image generated by the assistant video processor 13 to provide it to the assistant D2.

Figure 2:
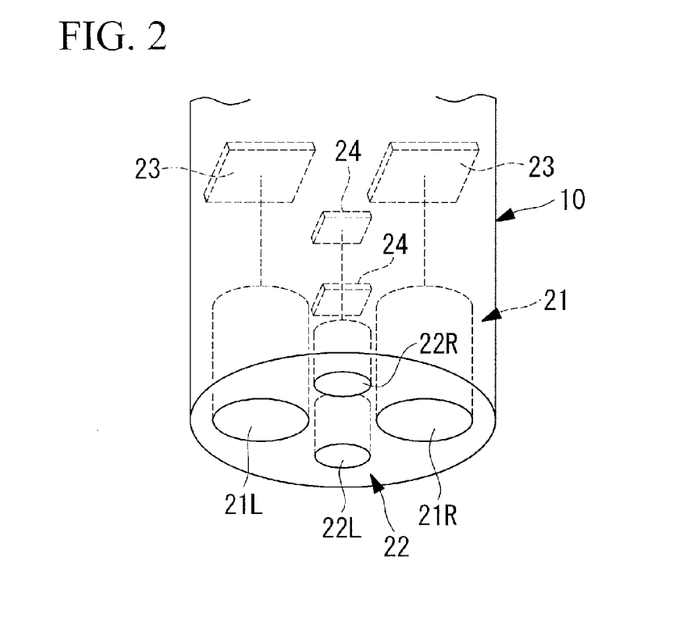
FIG. 2 is a diagram showing, in outline, the configuration of a case used in the surgical observation system according to the embodiment of the present invention.

As shown in FIG. 2, a first image-acquisition optical system 21 that obtains optical images of the surgical site T from the observation direction of the surgeon D1 (the direction of arrow A1 in FIG. 1) and a second image-acquisition optical system 22 that obtains optical images of the surgical site T from the observation direction of the assistant D2 (the direction of arrow A2 in FIG. 1) are built into the case 10.

More specifically, the first image-acquisition optical system 21 obtains, from the observation direction of the surgeon D1, a pair of optical images, having parallax, of the surgical site T via a pair of apertures 21L and 21R disposed side-by-side. The second image-acquisition optical system 22 obtains, from the observation direction of the assistant, where the angle about the optical axis differs from that of the observation direction of the surgeon, another pair of optical images, having parallax, of the surgical site T via another pair of apertures 22L and 22R disposed side-by-side.

The areas of the apertures 21L and 21R of the first image-acquisition optical system 21 are larger than the areas of the apertures 22L and 22R of the second image-acquisition optical system 22, and the first image-acquisition optical system 21 and the second image-acquisition optical system 22 are disposed so as to satisfy the following conditional expression.

$$0.4 \leq L2/L1 \leq 0.6 \tag{1}$$

Here, L1 is the distance between centers of the apertures of the first image-acquisition optical system, and L2 is the distance between centers of the apertures of the second image-acquisition optical system.

When the lower limit of conditional expression (1) is exceeded, the image quality when the optical image acquired by the second image-acquisition optical system is a three-dimensional image is considerably reduced, and thus it is not possible to perform observation well. When the upper limit of conditional expression (1) is exceeded, it becomes difficult to make the case 10 more compact. Therefore, by satisfying conditional expression (1), it is possible to make a distinction, such as providing a detailed image to the surgeon, who performs a precise procedure, and providing an image with the minimum required quality to the assistant, who performs an assistive procedure. Thus, it is possible to prevent a drop in the image quality due to the optical system itself becoming excessively small, and also, to position the image-acquisition optical systems with superior efficiency, which makes it possible to reduce the size of the housing accommodating the image-acquisition optical system.

The first image-acquisition optical system 21 and the second image-acquisition optical system 22 are configured so as to satisfy the following conditional expression.

$$1.5 \leq \beta 1/\beta 2 \leq 5 \tag{2}$$

Here, $\beta 1$ is the optical magnification of the first image-acquisition optical system 21, whereas $\beta 2$ is the optical magnification of the second image-acquisition optical system 22. It is also possible to employ a variable-magnification optical system in the first image-acquisition optical system 21 and the second image-acquisition optical system 22. In this case, $\beta 1$ and $\beta 2$ in conditional expression (2) are the optical magnifications of the entire system in the minimum-magnification states.

By satisfying conditional expression (2), it is possible to reduce the size of the image-acquisition optical systems while still maintaining the desired image quality, and therefore, it is possible to reduce the size of the housing accommodating the image-acquisition optical systems.

If the lower limit of conditional expression (2) is exceeded, the size-reduction effect of the second image-acquisition optical system relative to the first image-acquisition optical system is diminished, and size-reduction of the housing cannot be expected. Also, if the upper limit of conditional expression (2) is exceeded, the second image-acquisition optical system becomes too small relative to the first image-acquisition optical system. Only a small image-acquisition device having a small number of pixels can be applied to such an excessively small second image-acquisition optical system, and therefore, the image quality of the observation image obtained with the second image-acquisition optical system is degraded.

The surgical observation system includes first image-acquisition devices 23 that obtain a pair of images on the basis of the pair of optical images obtained by the first image-acquisition optical system 21, and second image-acquisition devices 24 that obtain another pair of images on the basis of the other pair of optical images obtained by the second image-acquisition optical system. The first image-acquisition devices 23 and the second image-acquisition devices 24 preferably satisfy the following conditional expression.

$$B \leq A/3 \tag{3}$$

Here, A is the image-acquisition region area of each first image-acquisition device 23, and B is the image-acquisition region area of each second image-acquisition device 24.

By satisfying conditional expression (3), it suffices to select the image-acquisition optical system according to the image-acquisition area of the image-acquisition device, and it is thus possible to select a second image-acquisition optical system that is more compact than the first image-acquisition optical system, while still maintaining the desired image quality; as a result, it is possible to reduce the size of the case accommodating the image-acquisition optical systems.

Next, Examples 1 to 3 of a wide-angle objective optical system according to the above embodiment will be described with reference to FIGS. 3 to 12. In the lens data given in each Example, r indicates the radius of curvature (unit: mm), d indicates the inter-surface distance (mm), Nd indicates the refractive index at the d-line, and Vd indicates the Abbe number at the d-line.

EXAMPLE 1

The relationship between the first image-acquisition optical system and the second image-acquisition optical system in a surgical observation system according to Example 1 of the present invention will be described below with reference to the drawings.

Figure 3:
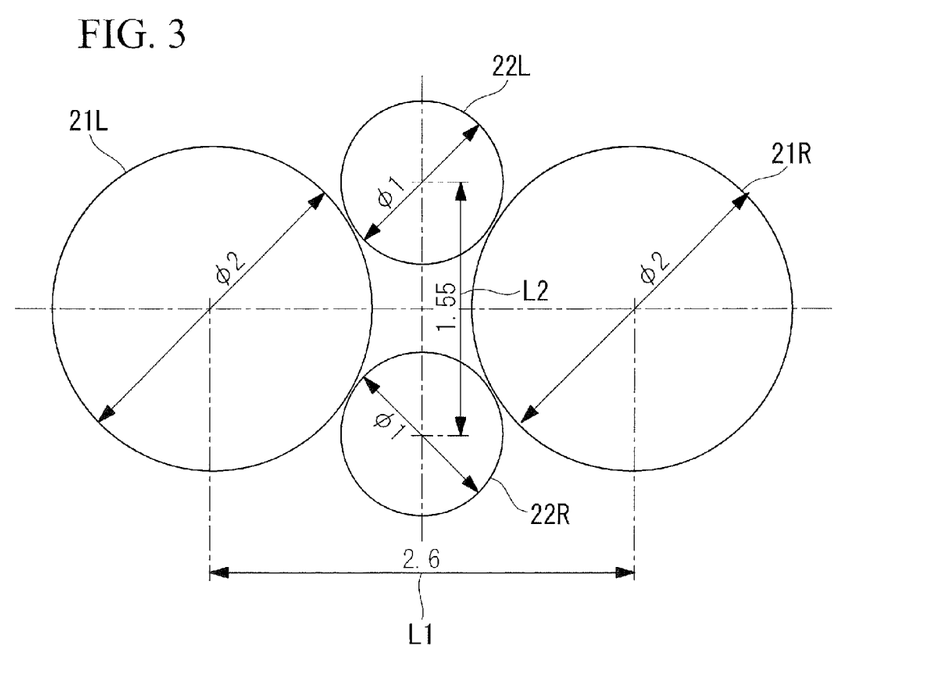
FIG. 3 is a diagram showing the positions of individual apertures of a first image-acquisition optical system and a second image-acquisition optical system in a surgical observation system of Example 1.
Figure 4:
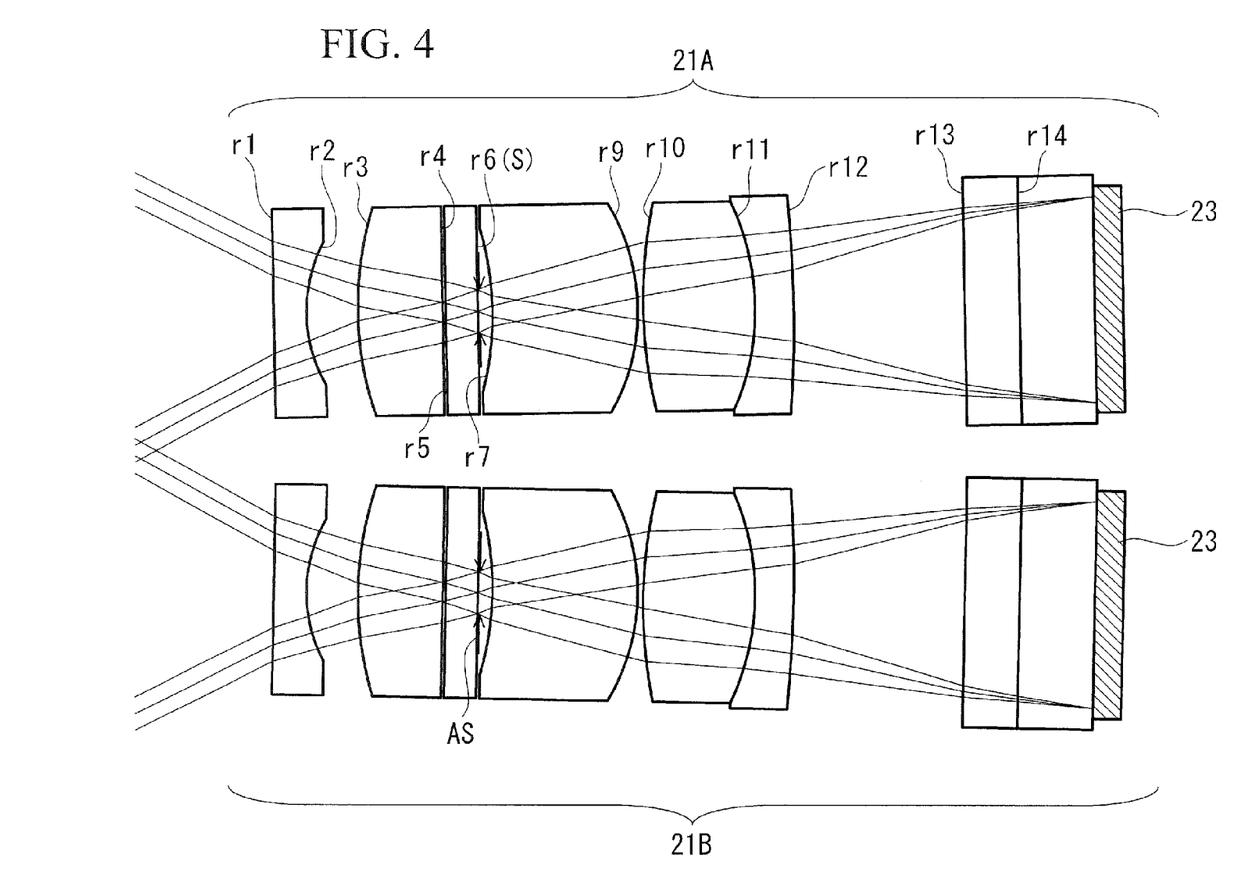
FIG. 4 is a sectional view showing the overall configuration of the first image-acquisition optical system in the surgical observation system according to Example 1.
Figure 5:
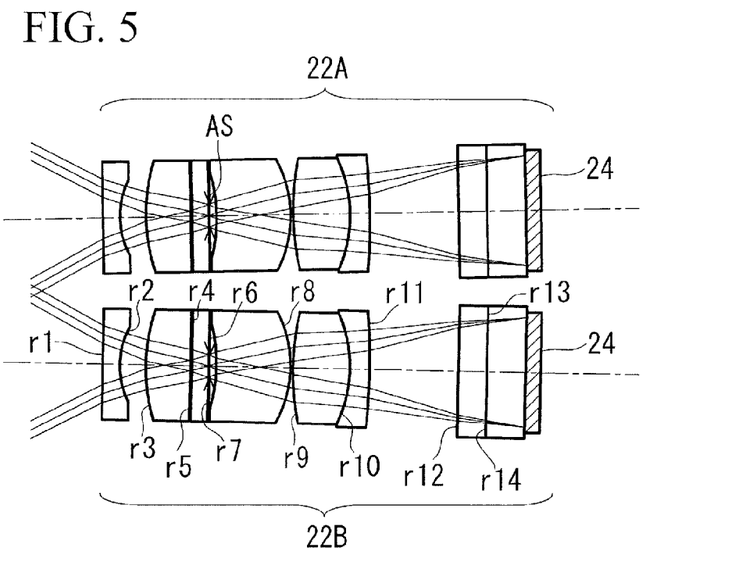
FIG. 5 is a sectional view showing the overall configuration of the second image-acquisition optical system in the surgical observation system according to Example 1.

FIG. 3 is a diagram showing the position of each aperture of the first image-acquisition optical system 21 and the second image-acquisition optical system 22, FIG. 4 is a sectional view showing the overall configuration of the first image-acquisition optical system, and FIG. 5 is a sectional view showing the overall configuration of the second image-acquisition optical system.

As shown in FIG. 4, the first image-acquisition optical system 21 is formed of an optical system 21A at the aperture 21L side and an optical system 21B at the aperture 21R side, and both optical systems 21A and 21B have the same configuration. In addition, the image-acquisition devices 23 are disposed at positions closest to image planes of the optical systems 21A and 21B, respectively.

Similarly, as shown in FIG. 5, the second image-acquisition optical system 22 is formed of an optical system 22A at the aperture 22L side and an optical system 22B at the aperture 22R side, and both optical systems 22A and 22B have the same configuration. In addition, the image-acquisition devices 24 are disposed at positions closest to the image planes of the optical systems 22A and 22B, respectively.

The lens data for the first image-acquisition optical system according to Example 1 of the present invention is shown below.

| Lens Data | | | | |
|---|---|---|---|---|
| Surface no. | r | d | Nd | Vd |
| Object plane | ∞ | 50 | | |
| 1 | ∞ | 0.3 | 1.517 | 52.43 |
| 2 | 1.4729 | 0.492 | | |
| 3 | 3.8081 | 0.786 | 1.883 | 40.77 |
| 4 | ∞ | 0.03 | | |
| 5 | ∞ | 0.3 | 1.521 | 74.98 |
| 6(stop) | ∞ | 0.13 | | |
| 7 | −3.3820 | 1.366 | 1.834 | 42.71 |
| 8 | −1.9090 | 0.05 | | |
| 9 | 4.8018 | 1.046 | 1.729 | 54.68 |
| 10 | −2.3941 | 0.35 | 1.923 | 18.90 |
| 11 | −13.8590 | 1.609 | | |
| 12 | ∞ | 0.5 | 1.516 | 64.14 |
| 13 | ∞ | 0.02 | 1.510 | 64.05 |
| 14 | ∞ | 0.7 | 1.611 | 50.49 |
| Image plane | | | | |

The lens data for the second image-acquisition optical system according to Example 1 of the present invention is shown below.

| Lens data | | | | |
|---|---|---|---|---|
| Surface no. | r | d | Nd | Vd |
| Object plane | ∞ | 50 | | |
| 1 | ∞ | 0.15 | 1.517 | 52.43 |
| 2 | 0.7365 | 0.246 | | |
| 3 | 1.9041 | 0.393 | 1.883 | 40.77 |
| 4 | ∞ | 0.015 | | |
| 5 | ∞ | 0.15 | 1.521 | 74.98 |
| 6(stop) | ∞ | 0.065 | | |
| 7 | −1.6910 | 0.683 | 1.834 | 42.71 |
| 8 | −0.9545 | 0.025 | | |
| 9 | 2.4010 | 0.523 | 1.729 | 54.68 |
| 10 | −1.1971 | 0.175 | 1.923 | 18.90 |
| 11 | −6.9295 | 0.783 | | |
| 12 | ∞ | 0.25 | 1.516 | 64.14 |
| 13 | ∞ | 0.01 | 1.510 | 64.05 |
| 14 | ∞ | 0.35 | 1.611 | 50.49 |
| Image plane | ∞ | | | |

Miscellaneous Data
L1=2.6 (mm)
L2=1.55 (mm)
β1=−0.041
β2=−0.02
A=0.543 (mm2)
B=0.176 (mm2)

Example 1 thus satisfies conditional expressions (1) to (3) above.

EXAMPLE 2

The relationship between the first image-acquisition optical system and the second image-acquisition optical system in a surgical observation system according to Example 2 of the present invention will be described below with reference to the drawings.

Figure 6:
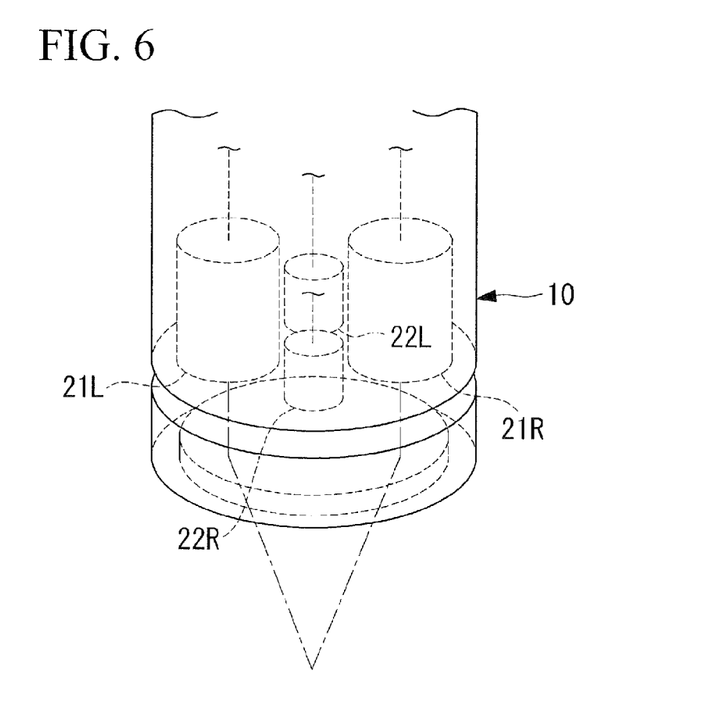
FIG. 6 is a diagram showing, in outline, the configuration of a case used in Example 2.
Figure 7:
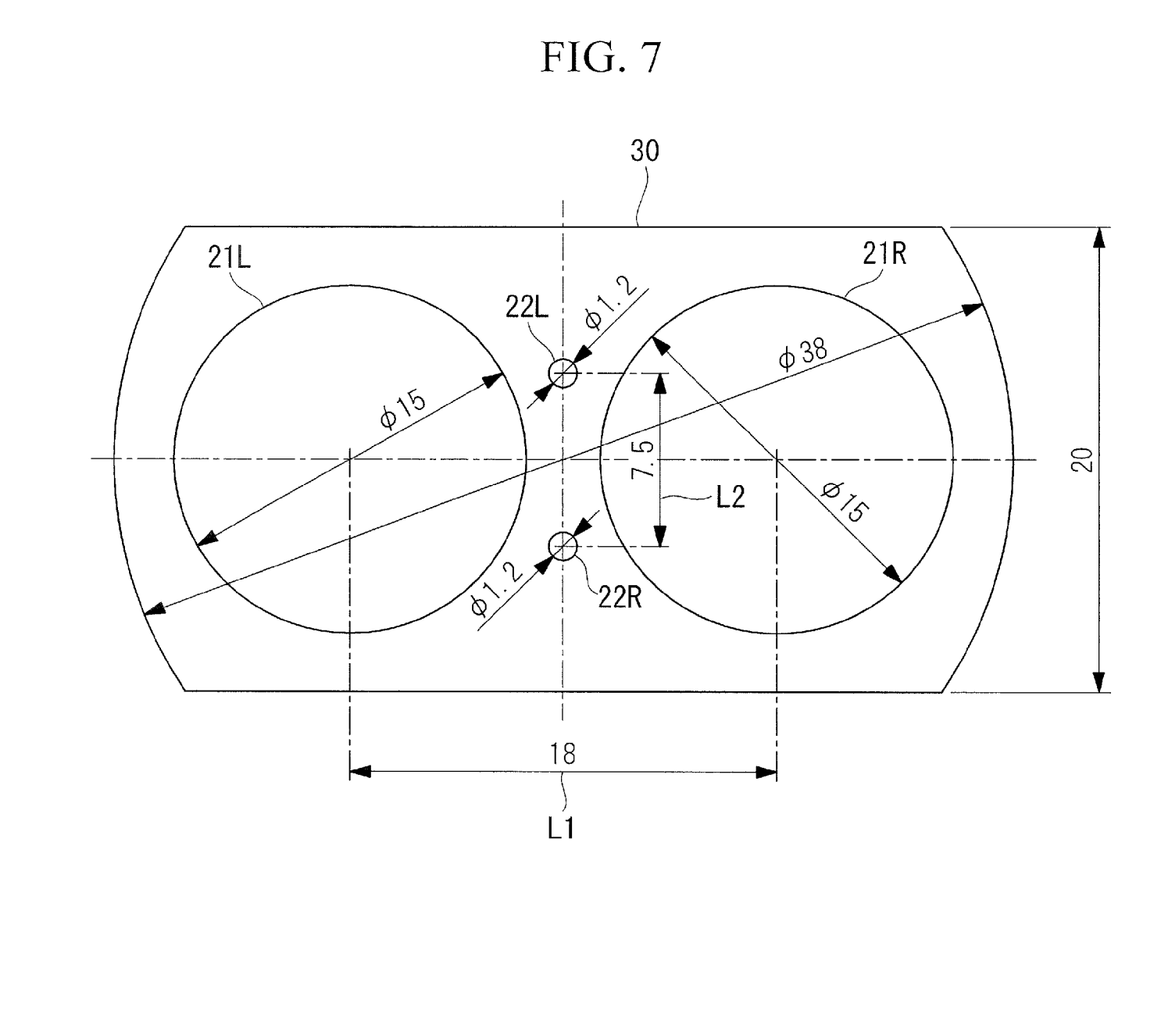
FIG. 7 is a diagram showing the positions of individual apertures of the first image-acquisition optical system and the second image-acquisition optical system in a surgical observation system of Example 2.
Figure 8:
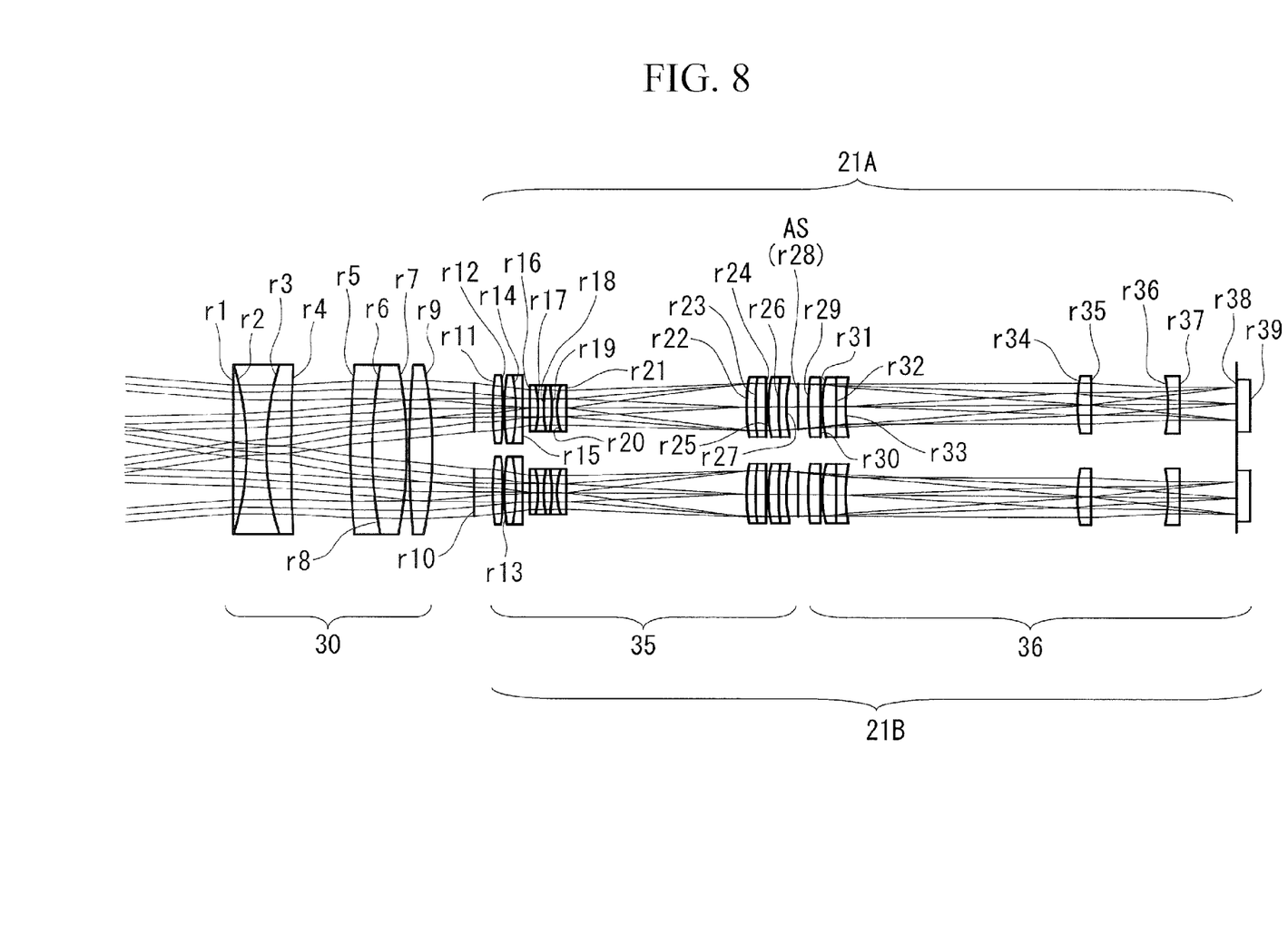
FIG. 8 is a sectional view showing the overall configuration of the first image-acquisition optical system in the surgical observation system according to Example 2.
Figure 9:
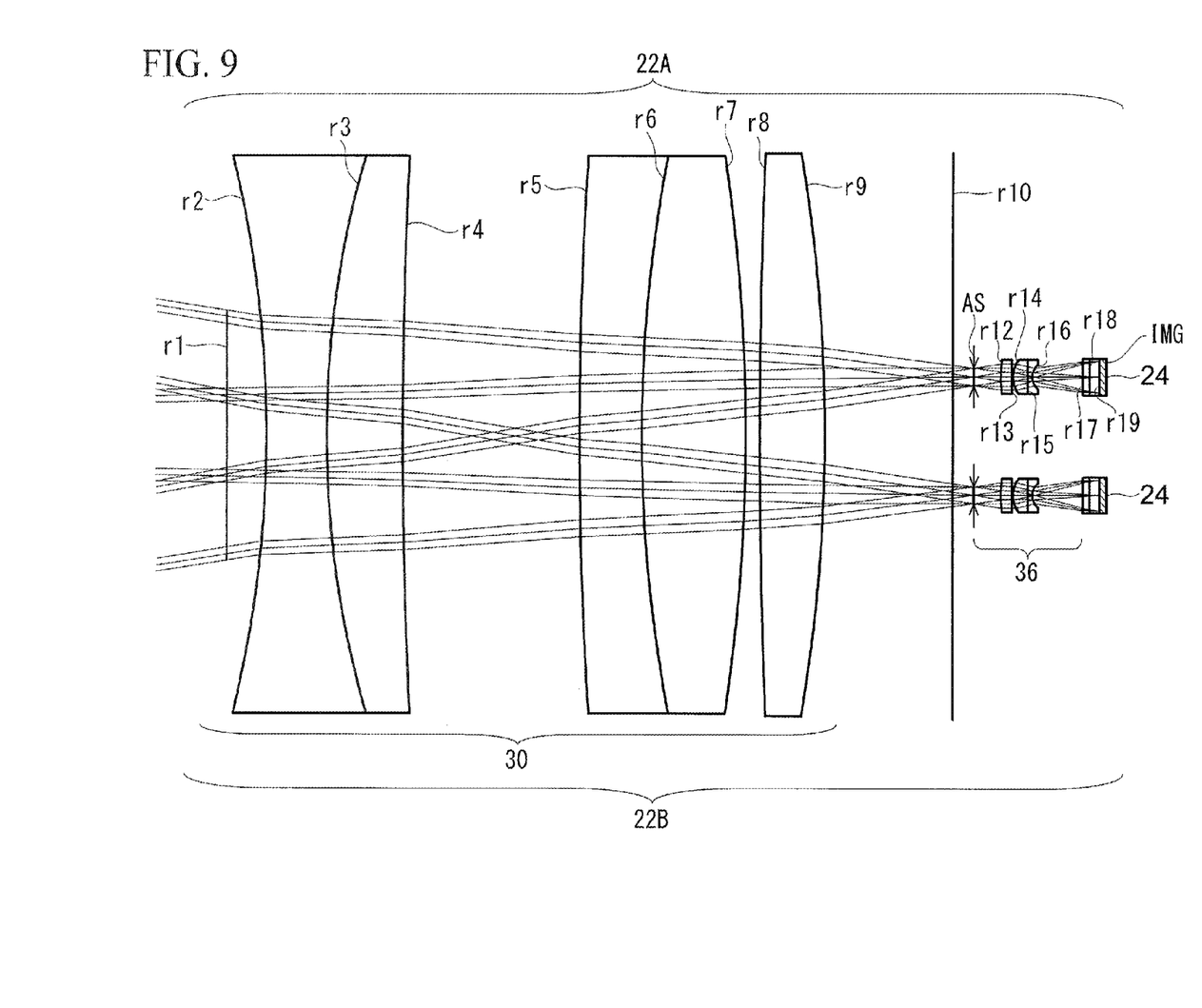
FIG. 9 is a sectional view showing the overall configuration of the second image-acquisition optical system according to Example 2.

FIG. 6 is a reference perspective view showing the case 10 which accommodates the first image-acquisition optical system 21 and the second image-acquisition optical system 22, FIG. 7 is a diagram showing the position of each aperture of the first image-acquisition optical system 21 and the second image-acquisition optical system 22, FIG. 8 is a sectional view showing the overall configuration of the first image-acquisition optical system, and FIG. 9 is a sectional view showing the overall configuration of the second image-acquisition optical system.

As shown in FIG. 8, the first image-acquisition optical system 21 is formed of an optical system 21A at the aperture 21L side and an optical system 21B at the aperture 21R side, and both optical systems 21A and 21B have the same configuration. The optical systems 21A and 21B are each formed of a collimating optical system 30, a variable-magnification optical system 35, and an image-forming optical system 36, which are described later. In addition, the image-acquisition devices 23 are disposed at positions closest to the image planes of the optical systems 21A and 21B, respectively.

Similarly, as shown in FIG. 9, the second image-acquisition optical system 22 is formed of an optical system 22A at the aperture 22L side and an optical system 22B at the aperture 22R side, and both optical systems 22A and 22B have the same configuration. In addition, the image-acquisition devices 24 are disposed at positions closest to the image planes of the optical systems 22A and 22B, respectively. The optical systems 22A and 22B are each formed of a collimating optical system 30 and an image-forming optical system 36, which are described later. In addition, the image-acquisition devices 24 are disposed at positions closest to the image planes of the optical systems 22A and 22B, respectively.

The collimating optical system 30, which converts the light incident via the apertures 21L, 21R, 22L, and 22R into collimated light, is provided at the incident end of the case 10 in the surgical observation system according to this Example. The collimating optical system 30 can be shared between the first image-acquisition optical system 21 and the second image-acquisition optical system 22, forming one part of the first image-acquisition optical system 21 and the second image-acquisition optical system 22.

Therefore, the collimating optical systems 30 shown in FIG. 8 and FIG. 9 are both the same optical system.

The lens data for the first image-acquisition optical system according to Example 2 of the present invention is shown below.

| Lens data | | | | |
|---|---|---|---|---|
| Surface no. | r | d | Nd | Vd |
| Object plane | ∞ | 300 | | |
| 1 | ∞ | 2.798 | | |
| 2 | −80.187 | 4.5 | 1.72 | 43.690 |
| 3 | 65.48 | 5.5 | 1.847 | 23.778 |
| 4 | 319.956 | 12.984 | | |
| 5 | 303.442 | 4.6 | 1.847 | 23.778 |
| 6 | 105.391 | 7.5 | 1.497 | 81.545 |
| 7 | −121.068 | 1.0 | | |
| 8 | 395.106 | 4.7 | 1.517 | 52.431 |
| 9 | −105.666 | 9.418 | | |
| 10 | ∞ | 3.969 | | |
| 11 | 66.506 | 2.0 | 1.439 | 94.95 |
| 12 | ∞ | 0.3 | | |
| 13 | 36.841 | 2.8 | 1.497 | 81.55 |
| 14 | −36.841 | 1.7 | 1.850 | 32.27 |
| 15 | −70.873 | 1.497 | | |
| 16 | −81.363 | 1.8 | 1.699 | 30.13 |
| 17 | −16.254 | 1.1 | 1.755 | 52.32 |
| 18 | 16.254 | 1.741 | | |
| 19 | −36.342 | 1.1 | 1.702 | 41.24 |
| 20 | 11.913 | 2.2 | 1.850 | 32.27 |
| 21 | ∞ | 39.893 | | |
| 22 | 77.747 | 1.5 | 1.702 | 41.24 |
| 23 | 36.015 | 2.7 | 1.497 | 81.54 |
| 24 | −57.889 | 0.3 | | |
| 25 | 29.81 | 2.4 | 1.755 | 52.32 |
| 26 | ∞ | 1.5 | 1.583 | 46.42 |
| 27 | 24.186 | 2.5 | | |
| 28(stop) | ∞ | 2.5 | | |
| 29 | 65.17 | 2.5 | 1.702 | 41.24 |
| 30 | ∞ | 0.5 | | |
| 31 | 29.719 | 3.0 | 1.497 | 81.55 |
| 32 | ∞ | 2.0 | 1.750 | 35.33 |
| 33 | 36.576 | 51.369 | | |
| 34 | 59.593 | 2.5 | 1.772 | 49.60 |
| 35 | ∞ | 17.042 | | |
| 36 | −30.998 | 2.5 | 1.596 | 39.24 |
| 37 | ∞ | 12.864 | | |
| 38 | ∞ | 0.5 | 1.510 | 63.00 |
| 39 | ∞ | 0.53 | | |
| Image plane | | | | |

The lens data for the second image-acquisition optical system according to Example 2 of the present invention is shown below.

| Lens data | | | | |
|---|---|---|---|---|
| Surface no. | r | d | Nd | Vd |
| Object plane | ∞ | 300 | | |
| 1 | ∞ | 2.798 | | |
| 2 | −80.187 | 4.5 | 1.72 | 43.690 |
| 3 | 65.48 | 5.5 | 1.847 | 23.778 |
| 4 | 319.956 | 12.984 | | |
| 5 | 303.442 | 4.6 | 1.847 | 23.778 |
| 6 | 105.391 | 7.5 | 1.497 | 81.545 |
| 7 | −121.068 | 1.0 | | |
| 8 | 395.106 | 4.7 | 1.517 | 52.431 |
| 9 | −105.666 | 9.418 | | |
| 10(stop) | ∞ | 1.5 | | |
| 11 | ∞ | 1.944 | | |
| 12 | 8.248 | 0.8 | 2.003 | 28.27 |
| 13 | ∞ | 0.111 | | |
| 14 | 2.049 | 1.0 | 1.816 | 46.62 |
| 15 | ∞ | 0.4 | 1.805 | 25.43 |
| 16 | 1.208 | 3.643 | | |
| 17 | ∞ | 0.5 | 1.516 | 64.14 |
| 18 | ∞ | 0.02 | 1.510 | 64.00 |
| 19 | ∞ | 0.7 | 1.610 | 50.30 |
| Image plane | | | | |

Miscellaneous Data
L1=18 (mm)
L2=7.5 (mm)
β1=−0.091
β2=−0.019
A=28.17 (mm2)
B=0.543 (mm2)

Example 2 thus satisfies conditional expressions (1) to (3) above.

EXAMPLE 3

The relationship between the first image-acquisition optical system and the second image-acquisition optical system in a surgical observation system according to Example 3 of the present invention will be described below with reference to the drawings.

Figure 10:
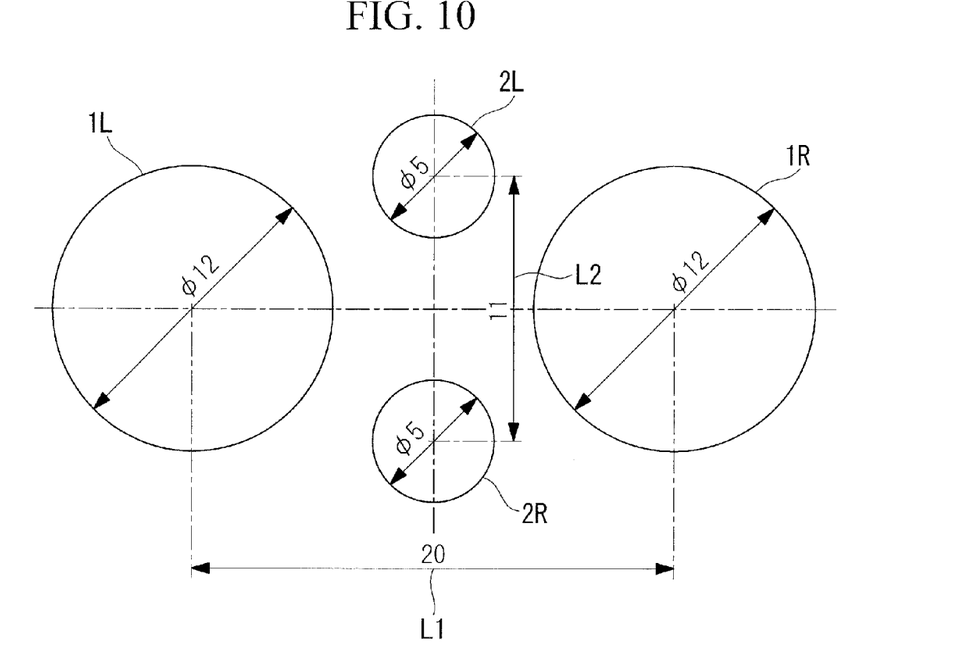
FIG. 10 is a diagram showing the positions of individual apertures of the first image-acquisition optical system and the second image-acquisition optical system in a surgical observation system of Example 3.
Figure 11:
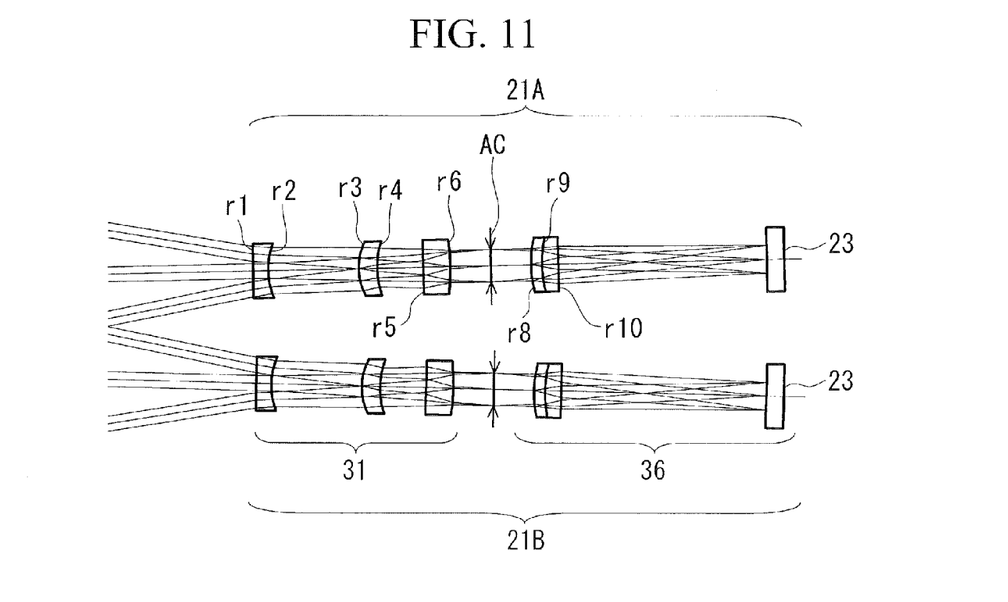
FIG. 11 is a sectional view showing the overall configuration of the first image-acquisition optical system in the surgical observation system according to Example 3.
Figure 12:
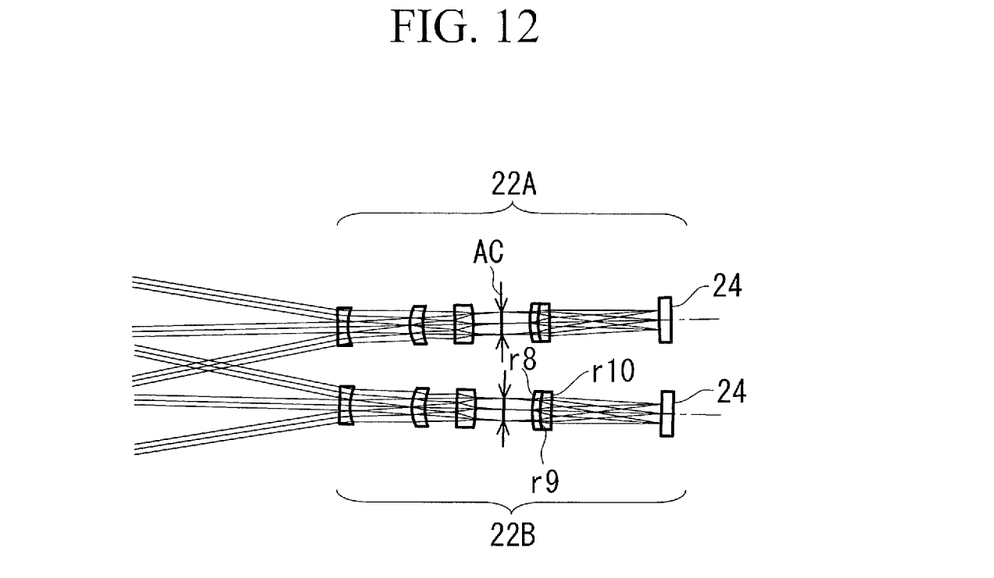
FIG. 12 is a sectional view showing the overall configuration of the second image-acquisition optical system in the surgical observation system according to Example 3.

FIG. 10 is a diagram showing the position of each aperture of the first image-acquisition optical system 21 and the second image-acquisition optical system 22, FIG. 11 is a sectional view showing the overall configuration of the first image-acquisition optical system, and FIG. 12 is a sectional view showing the overall configuration of the second image-acquisition optical system.

As shown in FIG. 11, the first image-acquisition optical system 21 is formed of an optical system 21A at the aperture 21L side and an optical system 21B at the aperture 21R side, and both optical systems 21A and 21B have the same configuration. In addition, the optical systems 21A and 21B are each formed of a collimating optical system 31 and an image-forming optical system 36. In addition, the image-acquisition devices 23 are disposed at positions closest to the image planes of the optical system 21A and 21B, respectively.

Similarly, as shown in FIG. 12, the second image-acquisition optical system 22 is formed of an optical system 22A at the aperture 22L side and an optical system 22B at the aperture 22R side, and both optical systems 22A and 22B have the same configuration. In addition, the image-acquisition devices 24 are disposed at positions closest to the image planes of the optical systems 22A and 22B, respectively. The optical systems 22A and 22B are each formed of a collimating optical system 31 and an image-forming optical system 36. In addition, the image-acquisition devices

24 are disposed at positions closest to the image planes of the optical systems 22A and 22B, respectively.

The lens data for the first image-acquisition optical system according to Example 3 of the present invention is shown below.

Lens Data

| Surface no. | r | d | Nd | Vd |
|---|---|---|---|---|
| Object plane | ∞ | 300 | | |
| 1 | 59.809 | 2.5 | 1.521 | 69.71 |
| 2 | 13.643 | 16.272 | | |
| 3 | 23.610 | 3.0 | 1.717 | 29.51 |
| 4 | 21.312 | 8.77 | | |
| 5 | ∞ | 5.0 | 1.575 | 41.49 |
| 6 | −30.399 | 8.0 | | |
| 7(stop) | ∞ | 8.0 | | |
| 8 | 63.025 | 1.5 | 1.717 | 29.51 |
| 9 | 15.108 | 4.0 | 1.640 | 60.10 |
| 10 | −38.155 | 42.957 | | |
| Image plane | | | | |

The lens data for the second image-acquisition optical system according to Example 3 of the present invention is shown below.

Lens Data

| Surface no. | r | d | Nd | Vd |
|---|---|---|---|---|
| Object plane | ∞ | 300 | | |
| 1 | 66.318 | 1.25 | 1.521 | 69.71 |
| 2 | 7.082 | 9.09 | | |
| 3 | 6.900 | 1.5 | 1.717 | 29.51 |
| 4 | 5.763 | 4.68 | | |
| 5 | ∞ | 2.5 | 1.575 | 41.49 |
| 6 | −13.188 | 4.0 | | |
| 7(stop) | ∞ | 4.0 | | |
| 8 | 19.390 | 0.75 | 1.717 | 29.51 |
| 9 | 5.646 | 2.0 | 1.640 | 60.10 |
| 10 | −15.792 | 15.227 | | |
| Image plane | | | | |

Miscellaneous Data
L1=20 (mm)
L2=11 (mm)
β1=−0.076
β2=−0.025
A=28.17 (mm2)
B=3.13 (mm2)

Example 3 thus satisfies conditional expressions (1) to (3) above.

Thus, since the above-described Examples each satisfy conditional expressions (1) to (3), with any of them, the housing can be made sufficiently compact while still allowing three-dimensional images to be acquired, and it is thus possible to prevent the housing from hindering the surgical procedure or viewing the monitors, which reduces the burden on the surgeon.

The above-described embodiment is derived from individual aspects of the present invention described below.

One aspect of the present invention is a surgical observation system including a first image-acquisition optical system that obtains, from a first observation direction, a pair of optical images, having parallax, of a subject via a pair of apertures disposed side-by-side; and a second image-acquisition optical system that obtains, from a second observation direction in which an angle about an optical axis differs from that of the first observation direction, another pair of optical images, having parallax, of the subject via another pair of apertures disposed side-by-side, wherein the areas of the apertures of the first image-acquisition optical system are larger than the areas of the apertures of the second image-acquisition optical system, and the first image-acquisition optical system and the second image-acquisition optical system are disposed so as to satisfy the following conditional expression.

$$0.4 \leq L2/L1 \leq 0.6 \tag{1}$$

Here, L1 is the distance between centers of the apertures of the first image-acquisition optical system, and L2 is the distance between centers of the apertures of the second image-acquisition optical system.

According to this aspect, because the observation directions of the surgeon and the assistant are different, and three-dimensional images as viewed from the direction of each person are provided, three-dimensional images of a surgical site from two different directions are obtained. At this time, the area of the aperture of the first image-acquisition optical system that obtains images from the first observation direction and the area of the aperture of the second image-acquisition optical system that obtains images from the second observation direction are different. By doing so, it is possible to make a distinction, such as, for example, providing a detailed image to the surgeon, who performs a precise operation, and providing an image with the minimum required image quality to the assistant, who performs an assisting operation. Accordingly, the overall area of the four apertures can be restricted.

In addition, by positioning the apertures so that the distance between the centers of the apertures of the first image-acquisition optical system and the distance between the centers of the apertures of the second image-acquisition optical systems satisfy conditional expression (1), it is possible to prevent a reduction in image quality caused by making the optical system too small, as well as to position the image-acquisition optical systems with superior efficiency, and it is possible to reduce the size of the housing that accommodates the image-acquisition optical system.

Therefore, the housing can be made sufficiently small while still allowing three-dimensional images to be obtained from two directions, so that the housing can be prevented from hindering the surgical procedure or viewing the monitor.

In the above aspect, the following conditional expression is preferably satisfied.

$$1.5 \leq \beta1/\beta2 \leq 5 \tag{2}$$

Here, β1 is an optical magnification of the first image-acquisition optical system, and β2 is an optical magnification of the second image-acquisition optical system.

By doing so, it is possible to reduce the size of the image-acquisition optical systems while still maintaining the desired image quality, and therefore, it is possible to reduce the size of the housing accommodating the image-acquisition optical systems.

The above-described aspect may further comprise first image-acquisition devices that obtain a pair of images on the basis of the pair of optical images obtained by the first image-acquisition optical system; and second image-acquisition devices that obtain another pair of images on the basis of the other pair of optical images obtained by the second image-acquisition optical system, wherein the following conditional expression is satisfied.

$$B \leq A/3 \tag{3}$$

Here, A is an image-acquisition region area of each first image-acquisition device, and B is an image-acquisition region area of each second image-acquisition device.

By doing so, it suffices to select the image-acquisition optical system according to the image-acquisition area of the image-acquisition device, and it is thus possible to select a second image-acquisition optical system that is more compact than the first image-acquisition optical system, while still maintaining the desired image quality; as a result, it is possible to reduce the size of the case accommodating the image-acquisition optical systems.

REFERENCE SIGNS LIST 10 case (housing)
12 surgeon video processor
13 assistant video processor
14 surgeon monitor
15 assistant monitor
21 first image-acquisition optical system
22 second image-acquisition optical system
23 first image-acquisition device
24 second image-acquisition device

The invention claimed is:

1. A surgical observation system comprising:
   a first image-acquisition optical system that obtains, from a first observation direction, a pair of optical images, having parallax, of a subject via a pair of apertures disposed side-by-side; and
   a second image-acquisition optical system that obtains, from a second observation direction in which an angle about an optical axis differs from that of the first observation direction, another pair of optical images, having parallax, of the subject via another pair of apertures disposed side-by-side,
   wherein areas of the apertures of the first image-acquisition optical system are larger than areas of the apertures of the second image-acquisition optical system, and the first image-acquisition optical system and the second image-acquisition optical system are disposed so as to satisfy the following conditional expression:

$$0.4 \leq L2/L1 \leq 0.6 \quad (1)$$

where L1 is a distance between centers of the apertures of the first image-acquisition optical system, and L2 is a distance between centers of the apertures of the second image-acquisition optical system.

2. The surgical observation system according to claim 1, wherein the following conditional expression is satisfied:

$$1.5 \leq \beta 1/\beta 2 \leq 5 \quad (2)$$

where $\beta 1$ is an optical magnification of the first image-acquisition optical system, and $\beta 2$ is an optical magnification of the second image-acquisition optical system.

3. The surgical observation system according to claim 1, further comprising:
   first image-acquisition devices that obtain a pair of images based on the pair of optical images obtained by the first image-acquisition optical system; and
   second image-acquisition devices that obtain another pair of images based on the other pair of optical images obtained by the second image-acquisition optical system,
   wherein the following conditional expression is satisfied:

$$B \leq A/3 \quad (3)$$

where A is an image-acquisition region area of each first image-acquisition device, and B is an image-acquisition region area of each second image-acquisition device.

* * * * *